United States Patent
Hartmann et al.

(10) Patent No.: US 10,529,453 B2
(45) Date of Patent: Jan. 7, 2020

(54) TOOL THAT ANALYZES IMAGE DATA AND GENERATES AND DISPLAYS A CONFIDENCE INDICATOR ALONG WITH A CANCER SCORE

(71) Applicant: Definiens AG, Munich (DE)

(72) Inventors: Kai Hartmann, Olching (DE); Florian Leiss, Munich (DE); Guenter Schmidt, Munich (DE)

(73) Assignee: Definiens GmbH, Munich (DE)

(*) Notice: Subject to any disclaimer, the term of this patent is extended or adjusted under 35 U.S.C. 154(b) by 178 days.

(21) Appl. No.: 15/663,819

(22) Filed: Jul. 31, 2017

(65) Prior Publication Data

US 2019/0034596 A1   Jan. 31, 2019

(51) Int. Cl.
*G16H 50/30* (2018.01)
*G06F 19/00* (2018.01)
(Continued)

(52) U.S. Cl.
CPC ............ *G16H 50/30* (2018.01); *A61B 5/4842* (2013.01); *G01N 33/574* (2013.01);
(Continued)

(58) Field of Classification Search
CPC ...... G16H 50/30; G16H 30/40; G06F 19/321; G06K 9/00147; G01N 33/574; G06T 7/0014; A61B 5/4842
(Continued)

(56) References Cited

U.S. PATENT DOCUMENTS

| | | | |
|---|---|---|---|
| 2007/0020646 A1* | 1/2007 | Hoon | C12Q 1/6886 435/6.11 |
| 2010/0023345 A1 | 1/2010 | Schottlander | G06Q 50/00 705/2 |

(Continued)

FOREIGN PATENT DOCUMENTS

| | | |
|---|---|---|
| WO | 2017/058848 A1 | 10/2015 |
| WO | WO2017/100541 | 12/2015 |
| WO | WO 2017058848 A1 * | 4/2017 ............... G06K 9/48 |

OTHER PUBLICATIONS

Extended European Search Report dated Jan. 3, 2019 in the counterpart foreign application EP18182459.0 issued by the European Patent Office (8 pages).

(Continued)

*Primary Examiner* — Ishrat I Sherali
(74) *Attorney, Agent, or Firm* — Imperium Patent Works; Darien K. Wallace

(57) ABSTRACT

A novel cancer scoring tool not only generates a score, but it also generates a confidence number. The tool receives a digital image of tissue of a patient. The tool identifies cell objects in the image and from that determines a first score. The magnitude of this first score is indicative of the severity of cancer in the tissue of the patient. The tool uses an overall false negative rate value and an overall false positive rate value to generate a set of second scores. The rate values are determined from training information. From the second scores, the tool determines the confidence number. The confidence number indicates the confidence the tool has in the first score being correct. The first score and an indication of the confidence number and the digital image are all displayed together on the display of the tool.

24 Claims, 8 Drawing Sheets

TRAINING PHASE

(51) Int. Cl.
*G06K 9/00* (2006.01)
*A61B 5/00* (2006.01)
*G01N 33/574* (2006.01)
*G06T 7/00* (2017.01)

(52) U.S. Cl.
CPC ....... *G06F 19/321* (2013.01); *G06K 9/00147* (2013.01); *G06T 7/0014* (2013.01)

(58) Field of Classification Search
USPC ........................................ 382/100, 128, 133
See application file for complete search history.

(56) References Cited

U.S. PATENT DOCUMENTS

| | | | |
|---|---|---|---|
| 2011/0312520 A1 | 12/2011 | Kennedy et al. | C12Q 1/68 506/9 |
| 2016/0110584 A1* | 4/2016 | Remiszewski | G06T 7/0012 382/133 |
| 2017/0084021 A1* | 3/2017 | Athelogou | G06T 7/0012 |
| 2018/0114317 A1* | 4/2018 | Song | G06K 9/6265 |
| 2018/0293728 A1* | 10/2018 | Daughton | A61B 5/7264 |

OTHER PUBLICATIONS

U.S. Appl. No. 15/075,180, filed Mar. 20, 2016, Harder et al.

* cited by examiner 0.5 MICRONS PER PIXEL

TRAINING IMAGE AS ANNOTATED BY AN EXPERT TO IDENTIFY CELLS

TRAINING PHASE 0.5 MICRONS PER PIXEL

DIGITAL IMAGE OF TISSUE OF THE PATIENT
(FOR DIAGNOSIS)

● = ORIGINAL CELL AS IDENTIFIED BY THE CELL IDENTIFICATION PROCEDURE

DIGITAL IMAGE OF THE TISSUE OF THE PATIENT WITH CELLS
IDENTIFIED BY THE CELL IDENTIFICATION PROCEDURE

● = ORIGINAL CELL AS IDENTIFIED BY THE CELL IDENTIFICATION PROCEDURE
○ = CELL ADDED
◯ = CELL SUBTRACTED

DIGITAL IMAGE OF THE TISSUE OF THE PATIENT WITH CELLS AS
IDENTIFIED BY THE CELL IDENTIFICATION PROCEDURE, WITH CELLS
ADDED, AND SOME IDENTIFIED CELLS SUBTRACTED

DIAGNOSTIC PHASE

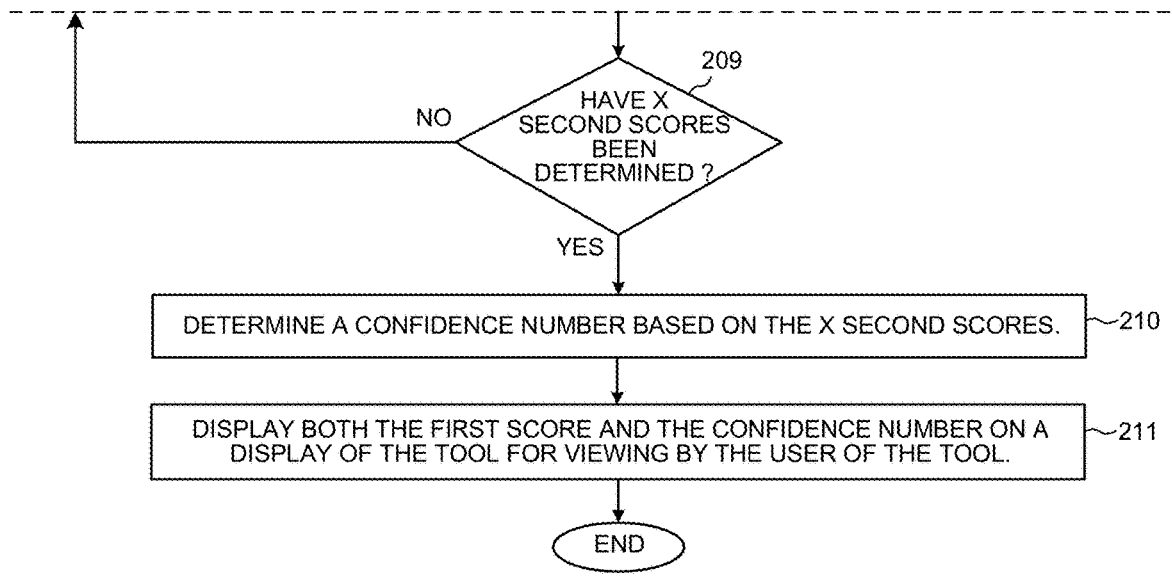
DIAGNOSTIC PHASE
FIG. 8B
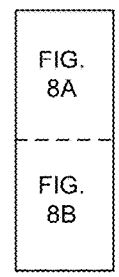
KEY TO FIG. 8
FIG. 8A
FIG. 8B
FIG. 8

TOOL THAT ANALYZES IMAGE DATA AND GENERATES AND DISPLAYS A CONFIDENCE INDICATOR ALONG WITH A CANCER SCORE

TECHNICAL FIELD

The present invention relates to systems and methods for detecting and diagnosing cancer.

BACKGROUND INFORMATION

In cancer detection and diagnosis, it is often useful to have a fast and reliable computerized method for analyzing slides of tissue from a patient, and for generating a score, where the score is indicative of the severity of cancer in the tissue, indicative of the probability of success of a particular treatment, or indicative of a subtype of cancer. U.S. Patent Application Publication number US2017/0084021, entitled "Grading of Glandular Tissue Cancer by Detailed Image Analysis of Stained Tissue Slices", published on Mar. 23, 2017, by Athelogou et al. sets forth an example of a system for generating one type a score. U.S. patent application Ser. No. 15/075,180, entitled "System for Predicting the Recurrence of Cancer in a Cancer Patient", filed on Mar. 20, 2016, by Harder et al. sets forth another example of a system for generating another type of score. Another example is described in WIPO published patent application number WO2017100541, entitled "Methods for Treatment and Selection of Patients Responsive to Immune Mediated Cancer Therapy", published on Jun. 15, 2017, by Binnig et al.

SUMMARY

A novel cancer scoring tool receives a digital image of tissue of a patient. The tool generates a score that is indicative of the severity of cancer in the tissue. The tool not only generates the score, but the tool also generates a confidence number. The tool first identifies cell objects in the image. The tool then uses information about these identified cell objects to determine a first score. The magnitude of this first score is indicative of the severity of cancer in the tissue of the patient. In addition, the tool stores an overall false negative rate value and an overall false positive rate value. The overall false negative rate value and the overall false positive rate value may, for example, be determined by the tool from training information. The tool uses the overall false negative rate value and the overall false positive rate value to generate a set of second scores. The tool then determines the confidence number based on the second scores. The confidence number indicates the confidence the tool has in the first score being correct. The notion of "correct" here is relative to expert annotations of the training information. The tool has a display. Both the first score and an indication of the confidence number are displayed together along with the digital image on the display. The confidence number can be displayed as a numerical value. Alternatively, the confidence number can be displayed as a graphical representation of a magnitude that does not involve a numeral.

Further details and embodiments and methods are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 8B is a second part of the larger FIG. 8.

DETAILED DESCRIPTION

Reference will now be made in detail to some embodiments of the invention, examples of which are illustrated in the accompanying drawings.

Figure 1:
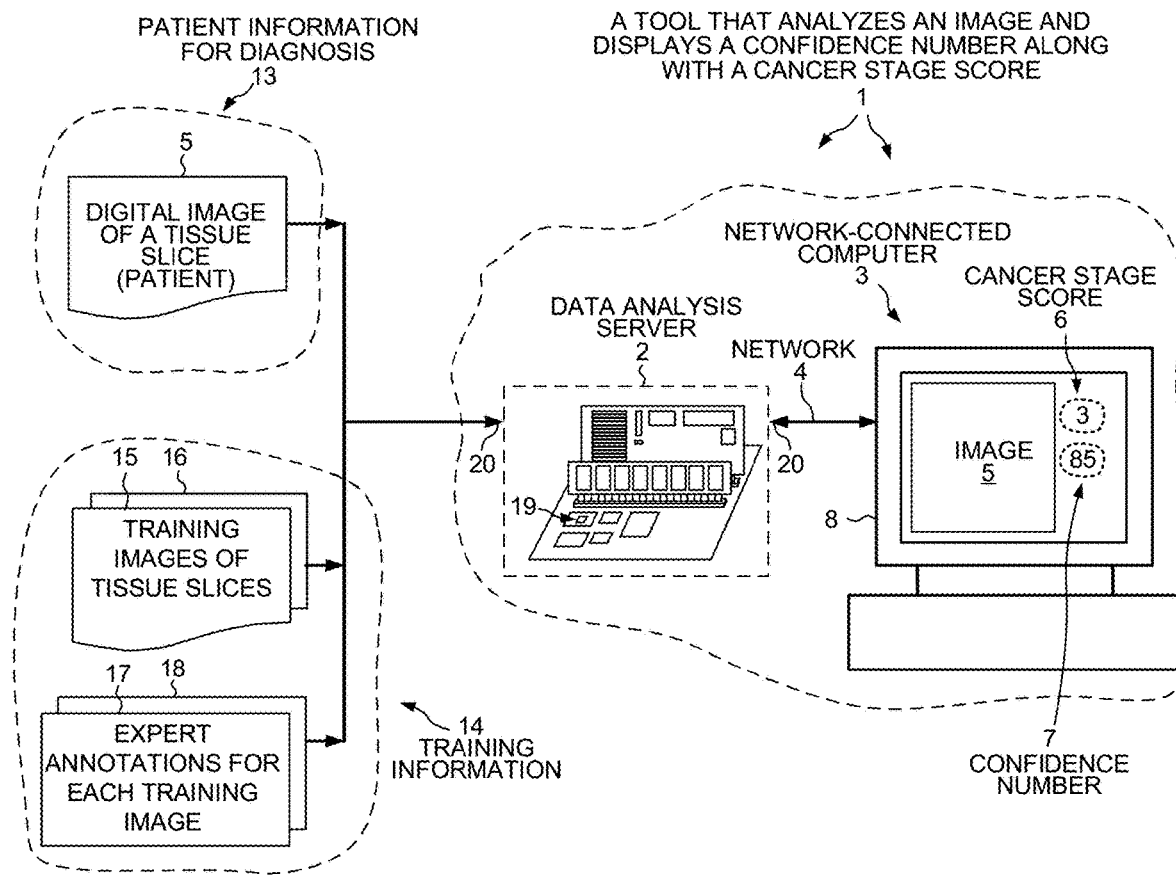
FIG. 1 is a conceptual diagram of a cancer scoring tool for analyzing a digital image.

FIG. 1 is a conceptual diagram of a cancer scoring tool 1. The tool 1 includes a server 2 and a network-connected computer 3. The network-connected computer 3 is coupled to the server 2 via one or more network connections and networking hardware 4. The network-connected computer 3 is generally not used for computation, but rather is used to view information prepared by the server 2 and to control and interact with software of the cancer scoring tool that is resident on the server 2. The tool 1 analyzes a high resolution digital image 5 of a stained slice of cancerous tissue of a cancer patient, and generates a score 6 and a confidence number 7. The digital image 5 is displayed on the graphical user interface display 8 of the network-connected computer 3 along with the score 6 and the confidence number 7. In the example of FIG. 1, the score is "3" and the confidence number is "85". The displayed score 6 is indicative of the severity of cancer. The displayed confidence number 7 is indicative of a confidence that the tool has in the score.

Figure 2:
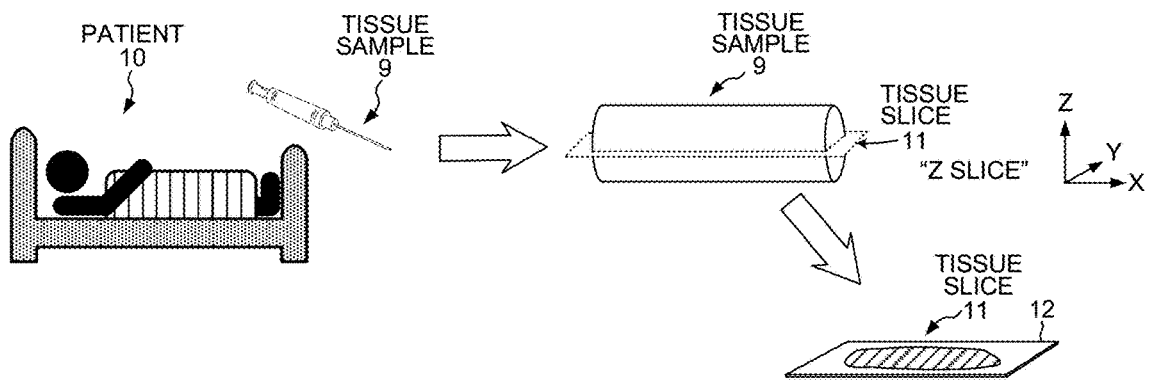
FIG. 2 illustrates one way that the digital image might be generated.

FIG. 2 illustrates one way that the digital image 5 might be generated. A tissue sample 9 is taken from the cancer patient 10. The tissue sample is sliced, thereby generating a tissue slice 11. The tissue slice 11 is stained with a biomarker such that non-cancerous cells tend to be stained blue whereas cancerous cells tend to be stained brown. The stained tissue slice is placed on a glass slide 12. A high resolution scanner then scans the slide, thereby generating a high resolution and high magnification digital image of the tissue sample. This is digital image 5 in FIG. 1. This digital image 5 is supplied as an input to the tool 1. The dashed circle to the left of FIG. 1 represents patient information for diagnosis 13. The digital image 5 is a part of that information. The digital image 5 is typically received onto the tool 1 from the scanner, either directly or via an intermediary computer, via an ethernet network port or USB port 20. If this is an ethernet network port, then it is typically the same network port via which the server 2 communicates with the internet in general, and with the network-connected computer 3.

In addition to the supplying of the digital image 5 to the tool 1, an amount of training information 14 is also supplied to the tool 1. This training information includes a set of high resolution and high magnification digital images of cancerous tissue. For each of these digital images, an expert at identifying cancer cells has generated a list of cancer cells. This is also referred to as "annotation". The expert is said to have "annotated" the image. For each cell that the expert identifies, the list includes position information indicating the X-Y position in the digital image where the expert had identified the cancerous cell. In FIG. 1, the training images are identified by reference numerals 15 and 16. The corresponding annotations are identified by reference numerals 17 and 18. Although only two training images and two annotations are illustrated in FIG. 1, there are actually many more pairs, where each pair includes an image and associated annotations. This training information is stored in the tool 1.

Figure 3:
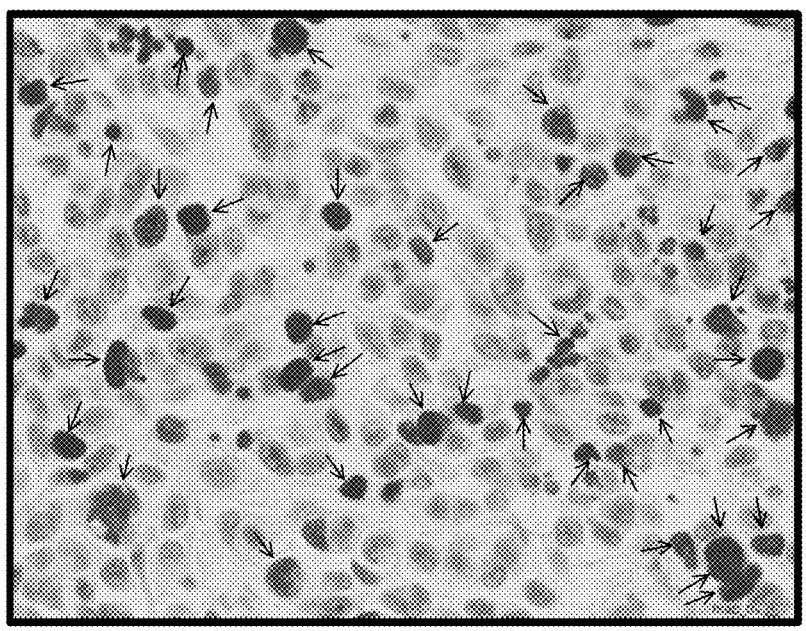
FIG. 3 illustrates a training image as annotated by an expert.

FIG. 3 illustrates training image 15 as annotated by an expert. The arrows indicate objects that the expert has identified to be cancer cells. For each identified cancer cell, the annotation information 17 includes X-Y position information indicating the location in the training image where the cell is found. In the training image of FIG. 3, the darker objects are cancer cells that are stained with a darker stain, namely a red stain. Red in the black and white of this patent document appears darker. The lighter objects are non-cancerous cells that are stained with a lighter stain, namely a blue stain. The lighter white in the background is an area where no cells of any type are found. Hematoxylin-stained cells (blue) in the black and white of this patent document appear as a lighter shade than the darker shade of the DAB-stained cells (brown). The training image is a digital image comprised of digital pixel data. The pixels of the image can be imagined to be organized in a two-dimensional array of rows and columns. The points in the training image represented by the pixel data are separated from one another in the vertical and horizontal dimensions by 0.5 microns.

The digital image 5 of the tissue of the patient, the training information 14, as well as cancer scoring tool software 19 is stored on server 2. The software 19 is a set of computer-readable instructions that is stored in a non-transitory manner on a computer-readable medium (for example, in semiconductor memory and/or on a magnetic hard disc) in the server 2. The tool 1, by virtue of a processor of its server 2 executing the software 19, generates and stores an "overall false positive rate value" and an "overall false negative rate value".

Figure 4:
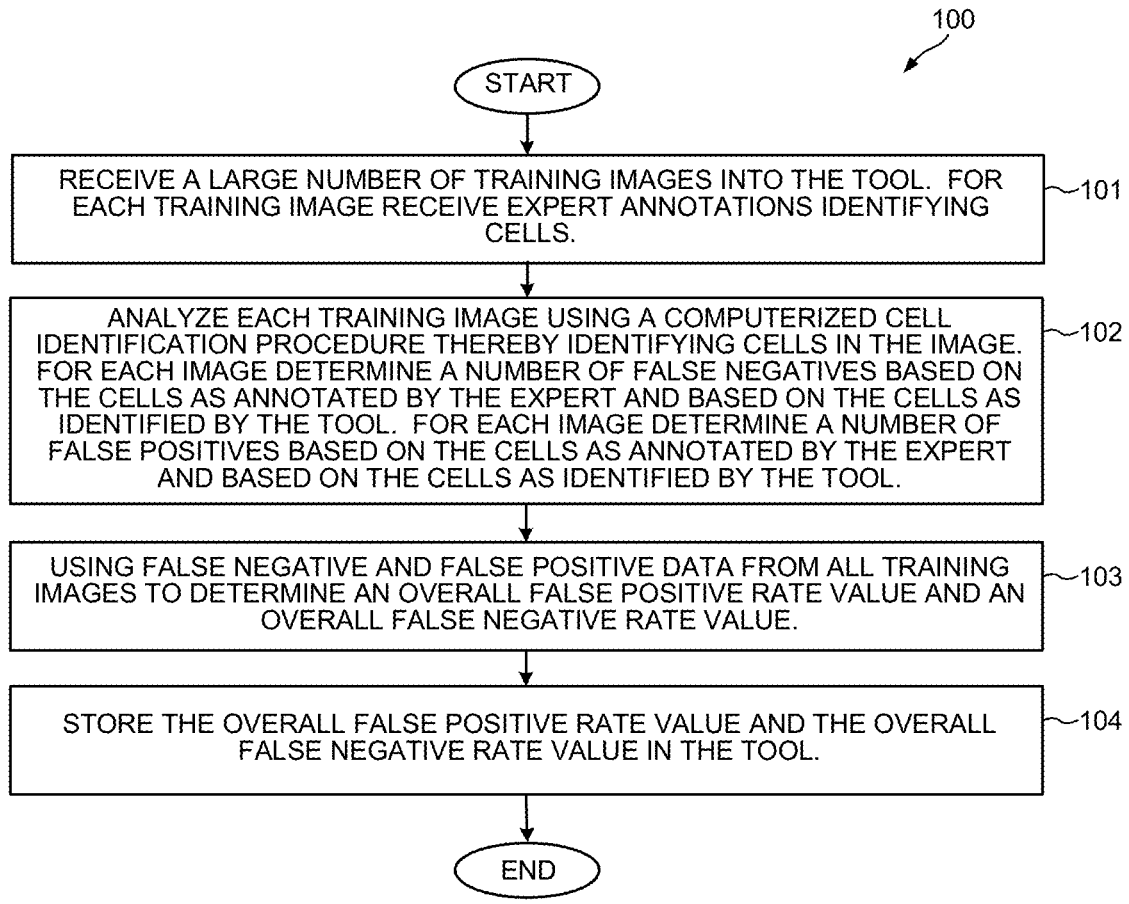
FIG. 4 illustrates a training phase method whereby the tool generates an overall false positive rate value and an overall false negative rate value.

FIG. 4 illustrates a training phase method 100 whereby the tool 1 generates the overall false positive rate value and the overall false negative rate value in more detail. First, the large number of training images is received (step 101) into the tool. For each training image, expert annotation information identifying cells is also received into the tool. Next, each of the training images is analyzed (step 102) by the tool, thereby identifying cell objects in the image. This computerized identification of cell objects is done as follows. A color deconvolution algorithm is applied to the training image in order to separate blue pixels from brown pixels. Two images are generated. The first is a grey-scale image that is an intensity map of the blue. The second is a grey-scale image that is an intensity map for brown. Each pixel in the grey-scale image for brown has a value in a range from 0 to 255. A so-called "brown pixel value threshold" is then applied to the grey-scale image for brown. The brown pixel value threshold is set to be 100. Pixels having values of 100 or more are considered brown. Pixels having values under 100 are considered not to be brown. The grey-scale image for brown is therefore converted into what can be considered to be a black and white image for brown. Black in this black and white image represents pixels determined to be brown. White in this black and white image represents pixels determined not to be brown.

Next, the tool analyzes the thresholded black and white image to identify cell objects. Initially, all adjoining brown pixels are determined to be an object. If there is a ring of brown pixels that is nearly closed, then a close algorithm is applied. This close algorithm changes pixels in the gap to be brown pixels. Then any brown pixels that form a loop where the look contains a non-brown pixel are identified. A fill algorithm is applied to switch these non-brown pixels to be brown pixels. Next, a watershed algorithm is applied to find and to split certain types of objects. For example, objects that have the shape of an eight, or an hour glass, are broken into two cell objects. At this point in the process, each different set of connected brown pixels is determined to be a different object. Such an object is also referred here as a cell or a cell object. A cell object typically has a round or oval shape, and is about ten microns in diameter. At an image resolution of 0.5 microns per pixel, the typical cell object is about twenty pixels across. Each different cell object is given a unique identifier. The X-Y coordinates of the center of the cell object is stored in association with the object identifier. The result is a list of cell objects. Each entry in the list is for a different cell object. Each entry in the list includes a unique object identifier and a position value.

The tool then compares the list of cell objects in the training image as identified by the tool to the list of cells that the expert identified in the training image. The list of cells that the expert identified in the training image is, as explained above, in the annotation information stored in association with the training image. The expert is considered to be correct in identifying a cell. Also, when the expert examines an area of a training image and determines that no cell should be identified in that area, this decision not to identify a cell is also considered to be correct. The number of cell objects that the tool identified in the training image as cells that the expert did not identify as cells is logged. These cell objects are referred to as "false positive cells". Also, the number of cells that the expert did identify but that the tool improperly failed to identify as cell objects is logged. These cells are referred to as "false negative cells". The number of false positive cells per hundred properly identified cell objects is determined and is stored as the false positive rate value for the training image. The number of false negative cells per hundred properly identified cell objects is determined and is stored as the false negative rate value for the training image. This process is repeated for each of the training images. In this way, for each training image, the tool generates a false positive rate value and a false negative rate value.

Next, the tool uses (step 103) all the false positive rate values to generate one "overall false positive rate value". This overall false positive rate value may, for example, be an average of all the false positive rate values for the training images. Likewise, the tool uses all the false negative rate values to generate one "overall false negative rate value". This overall false negative rate value may, for example, be an average of all the false negative rate values for the training images. Once determined, the overall false positive rate value and the overall false negative rate value are stored (step 104) in the tool.

Figure 5:
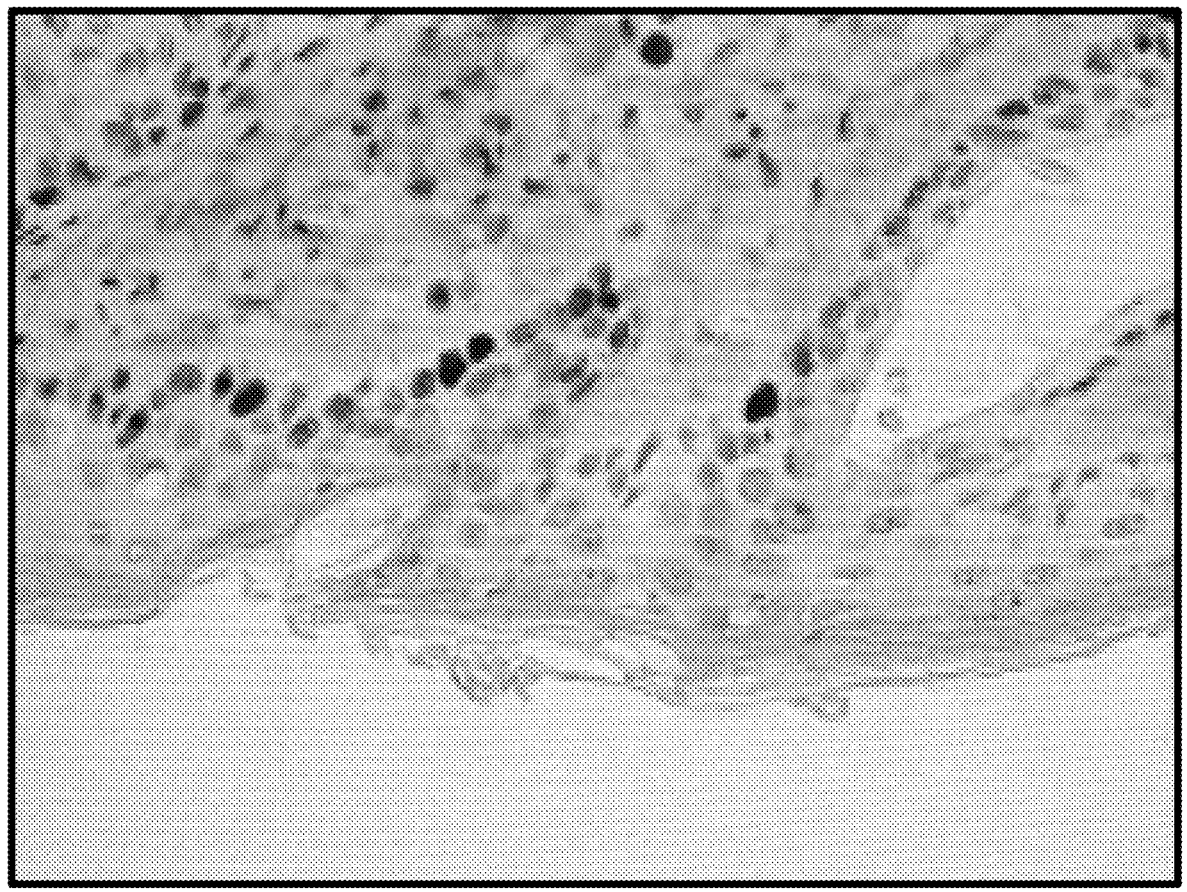
FIG. 5 illustrates the digital image of the stained tissue of the patient.

FIG. 5 illustrates the digital image 5 of the stained tissue of the patient. Next, the tool analyzes the digital image 5 to identify cell objects. The process is the same as described above in connection with the tool analyzing training images to identify cell objects. Accordingly, the tool generates a list of identified cell objects for the digital image 5 of the patient. This list is referred to here as the "first information".

Figure 6:
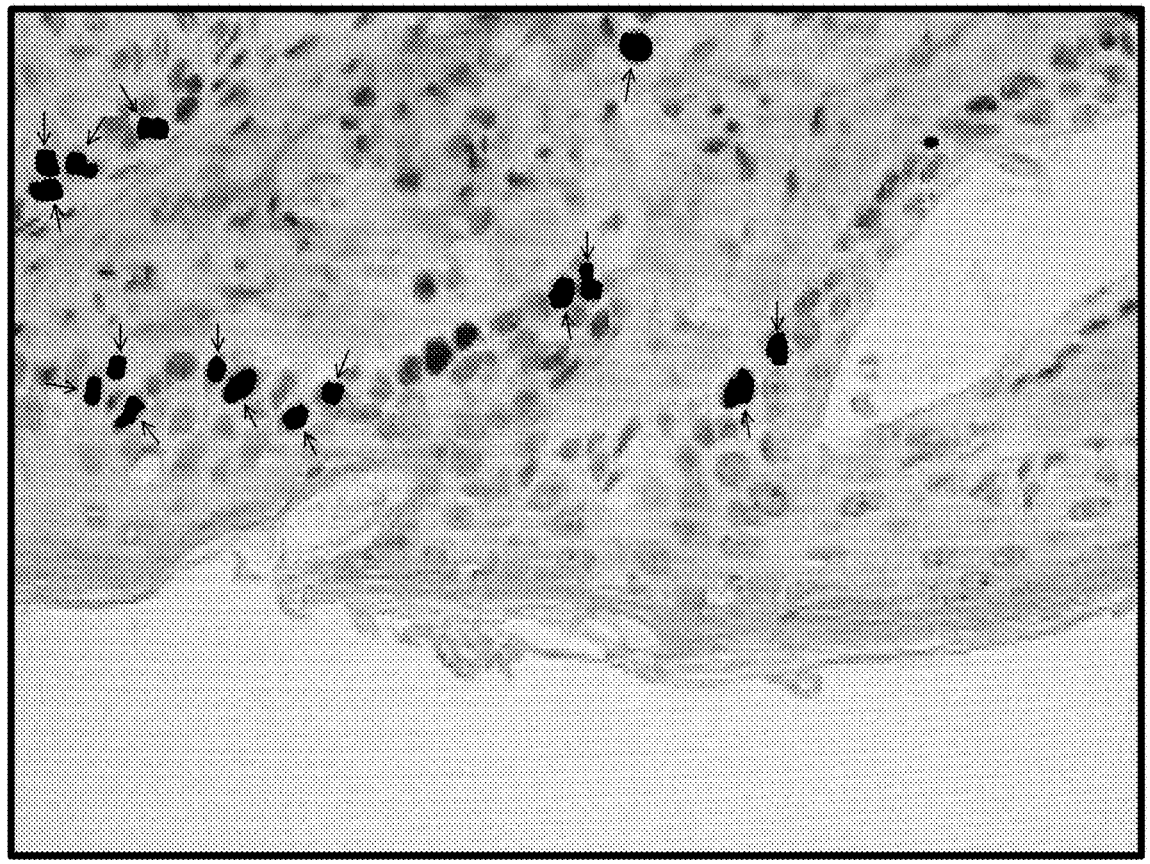
FIG. 6 illustrates the result of applying the cell identifying process on the digital image of FIG. 5.

FIG. 6 illustrates the result of the cell identifying process. Each arrow in FIG. 6 marks an identified cell object. The identified cell objects have been darkened.

Next, the tool determines a score based on the first information. This score is referred to as the "first score". A score can have one of four possible score values: "1", "2", "3" and "4". A score of "1" indicates a low severity of cancer. A score of "4" indicates a high severity of cancer. The tool considers each 50 micron by 50 micron square area (100 pixel by 100 pixel square area) of the image. The tool determines the number of identified cells in that square area. The number is recorded. The square area of interest is then shifted across the image slightly, and the number of identified cells in the shifted area is determined and recorded. This process is repeated with the square area of interest being panned across the image in both the X and the Y dimensions. For each new location of the square area of interest a different cell object count is made and stored. Once the entire image 5 has been panned in this way, the highest one of these cell object counts is identified. This highest count value, because it is a count of cell objects, is an integer. Four ranges of cell object counts are considered. In one example, the first range is a cell object count of 0; the second range is a cell object count of 1 to 5; the third range is a cell object count of 6 to 10; and the fourth range is a cell object count of 11 or more. If this highest count value is in the first range, then the score is 1. If this highest count value is in the second range, then the score is 2. If this highest count value is in the third range, then the score is 3. If this highest count value is in the fourth range, then the score is 4. In this way, a first score is determined based on the first information. This "first score" is the score 6 that will be displayed to the user as explained in further detail below.

Next, the tool multiplies the overall false negative rate value by the total number of cell objects found in the image, thereby generating a first number of cell objects. This first number is an additional number of cell objects that were not identified in the image by the tool but perhaps should have been identified as indicated by the training information.

Next, the tool multiplies the overall false positive rate value by the total number of cell objects found in the image, thereby generating a second number of cell objects. This second number is a number of the identified cell objects that may have been falsely identified to be cell objects when they in fact they should not have been so identified. The first number and the second number are stored in the tool in association with the digital image 5.

The tool then repeats the above described process of analyzing the digital image 5, except in this second pass the brown pixel value threshold is reduced. Reducing the brown pixel value threshold causes more pixels to be determined to be brown. Because more pixels are determined to be brown, more cell objects will be identified. The cell objects that were identified in this second pass but that were not identified in the first pass are recorded in a cell candidate list. Each is assigned a unique cell identifier and position information is stored for each.

A number of the cell objects in the cell candidate list is then added to the cell list for the first pass in order to make a cell list for the second pass. The number of cell objects that are added in this way is the first number. Which particular ones of the cell objects in the cell candidate list it is that are added is randomly determined. The result is that the cell list for the second pass now includes information on the added cell objects.

Figure 7:
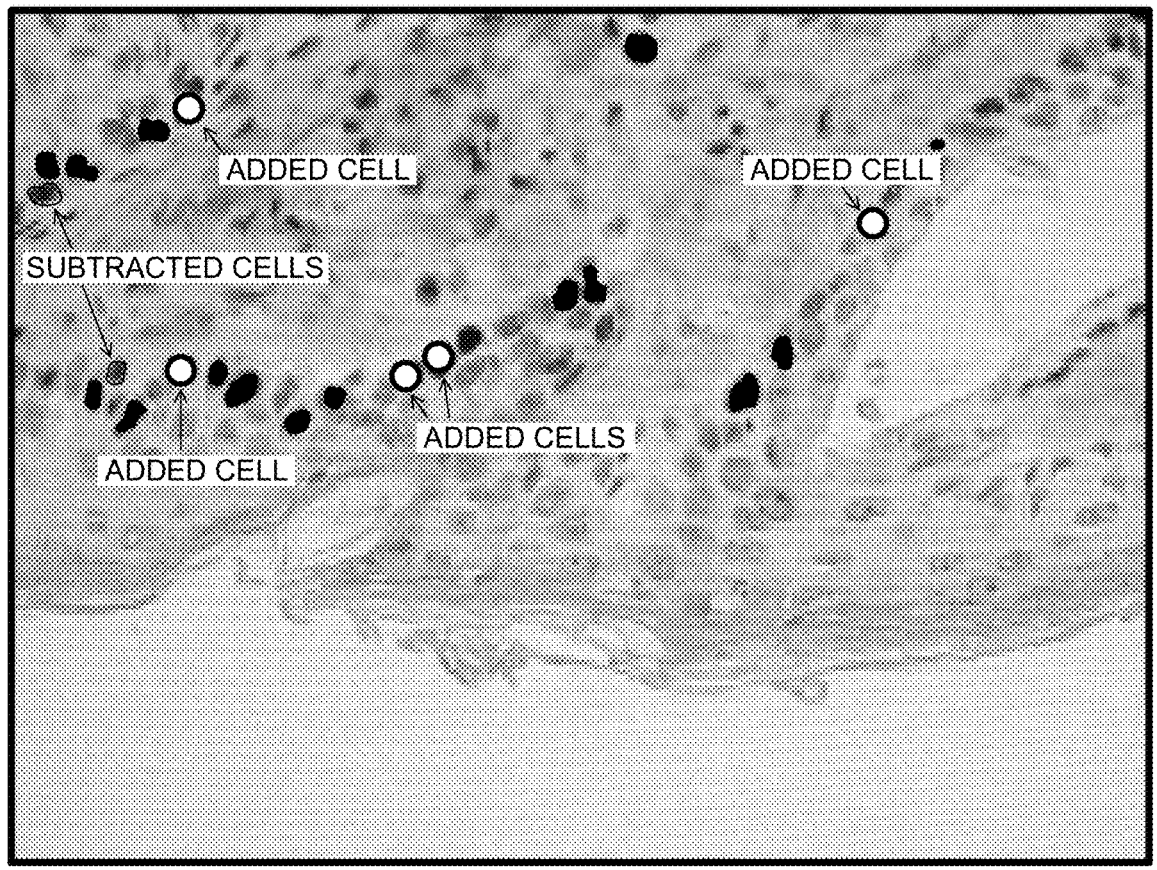
FIG. 7 illustrates the adding of cell objects and the subtracting of cell objects.

FIG. 7 illustrates this adding of cell objects. Cell objects that were added are denoted in the diagram with the text "ADDED CELLS" or "ADDED CELL". Note that each added cell was added at a candidate cell location where it appears, from inspection of the image, that a cell could have been identified in the first cell-identifying pass. These sites where cell objects can be added are sites of cell objects in the cell candidate list. The candidate cell object sites are due to the reducing of the brown pixel value threshold for this second pass.

Next, some of the cell objects that were identified in the first pass are subtracted from the second cell list. The number of cells that is subtracted is the second number. Which particular ones of the previously identified cell objects (cell objects identified in the first pass) it is that are subtracted in this way is random. In the present example, two cell objects are subtracted. The corresponding cells that are subtracted are identified in FIG. 7 with the text "SUBTRACTED CELLS". The result of the adding of cell objects and the subtracting of cell objects is a final cell object list for the second pass. This list is then scored using the same scoring method described above. The resulting score is referred to as a "second score". The second score for the second pass is stored in a list of second scores.

The tool then repeats the process of generating a second score. In this next pass, different cell objects are added to the cell objects identified in the first pass. Which particular ones of the cell objects from the cell candidate list it is that are added is random. Also, different ones of the cell objects identified in the first pass are subtracted. The resulting next list of cell objects is then scored, thereby generating another second score. This second score is added onto the list of second scores.

The tool repeats this process of generating second scores many times. In the present example, the tool repeats this process one hundred times such that one hundred second scores are generated.

Next, the tool determines a confidence number based on the list of second scores and based on the first score generated in the first pass. This confidence number is the confidence number 7 illustrated in FIG. 1. In the present example, the confidence number is a value in the range from 0 to 100. It is the number of second scores in the list of one hundred second scores that exactly match the first score generated in the first pass. A confidence number of zero would mean that none of the second scores matched the first score determined in the first pass. A confidence number of 100 would mean that all one hundred of the second scores matched the first score determined in the first pass.

Lastly, the tool 1 displays both the confidence number 7 as well as the first score 6 (the score generated on the first pass) on the display 8. These values are displayed together on the display 8 along with the digital image 5 of the tissue of the patient. FIG. 1 illustrates on way that the information may be displayed. The first score 6 is the score determined by the tool for the digital image 5. This is a number from 1 to 4 that indicates the severity of cancer. The confidence number 7 is a number from 0 to 100. It indicates a confidence that the tool has in the displayed score. Alternatively, the tool 1 displays the confidence number as a distribution of second scores. It may suggest an alternative score based on this distribution.

Figure 8A:
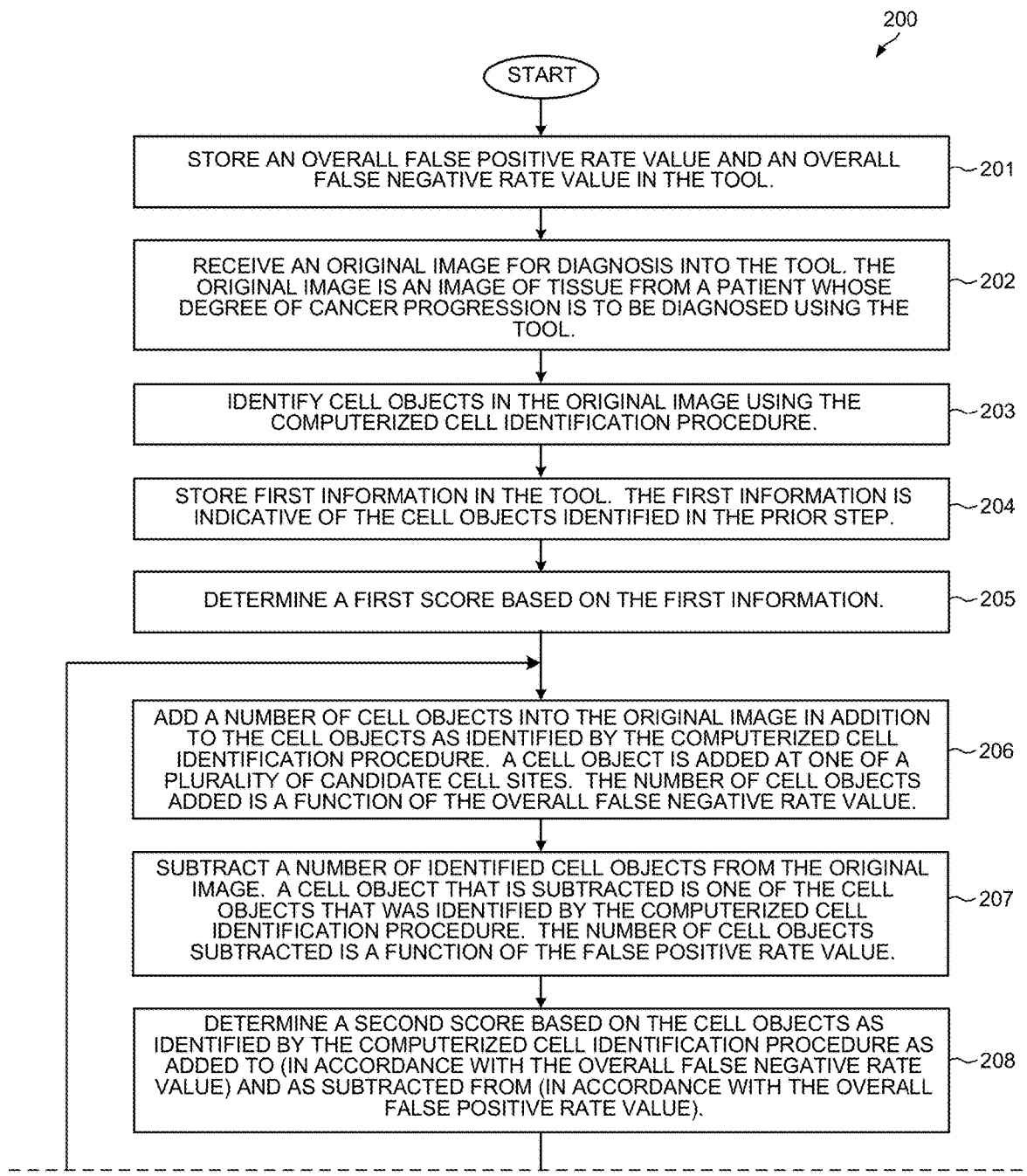
FIG. 8A is a first part of a larger FIG. 8, where the larger figure sets forth a flowchart of a novel diagnostic phase method.

FIG. 8A and FIG. 8B together form a larger figure, FIG. 8. FIG. 8 is a flowchart diagram of a diagnostic phase method 200 in accordance with one novel aspect. This flowchart presents the method described in the text above, but in flowchart form. In a first step (step 201), the overall false positive rate value and the overall false negative rate value are stored in the tool. One way of generating the overall false positive rate value and the overall false negative rate value is set forth in FIG. 4. Next (step 202), the original digital image of patient tissue is received into the tool. In the explanation above, this is digital image 5. Next (step 203), the tool analyzes the digital image 5 and identifies cell objects. As explained above, a list of cell objects is developed. Each entry in the list includes a cell object identifier as well as position information. This list is also referred to as "first information". This first information is stored (step 204) in the tool in association with the original digital image 5. Next (step 205), the tool scores the first information, thereby generating a first score. This is the first pass described in the example set forth above. After this first pass has resulted in the generation of the first information and the first score, a second pass is made. In the second pass, the list generated in the first pass (the "first information") is used as a starting point. A number of cell objects is then added (step 206) to this list. This adding is also somewhat colloquially described as the adding of cell objects into the image. Each added cell object is added at a selected one of a plurality of candidate cell sites. The number of cell objects added (the first number) is a function of the overall false negative rate value. Next (step 207), a number of the cell objects that were identified in the first pass is subtracted from the cell object list. The number of cell objects subtracted (the second number) is a function of the overall false positive rate value. This subtracting is also colloquially described as the subtraction of cells from the image. The result of this adding (step 206) of cell objects and this subtracting (step 207) of cell objects is what is referred to here as "second information". Although the adding is described here as occurring before the subtracting, the subtracting can be done before the adding. The order of steps 206 and 207 can be reversed. The second information in the example explained above is a list of cell objects for the second pass. Next, the tool determines a second score (step 208) based on the second information (the cell objects in the list for the second pass). The resulting second score is recorded in a list of second scores. Steps 206, 207 and 208 are repeated a number of times. For each such second pass, another second score is generated. The second score is added to the list of second scores. In the example described above, one hundred second scores are determined. When a predetermined number of second scores has been determined (step 209), the tool determines a confidence number (step 210) based on the second scores. In the example described above, if one hundred second scores are determined, then the confidence number is the number of those second scores that match the first score. The tool then displays (step 211) both an indicator of the first score and an indicator of the confidence number on the display 8 of the tool 1 for viewing by the viewer. In one example, this involves communicating the indictor of the confidence number and the indictor of the first score as part of a network packet. The network packet is received by the network-connected computer 3. The network-connected computer 3 then displays the indictor of the confidence number and the indictor of the first score on the display 8. The indicator of the first score may be a number as in the example illustrated in FIG. 1, or it may be another type of graphical representation of the first score. The indicator may be a graphical magnitude bar whose length indicates the score of 1 to 4 in a graphical way without the use of numerals. Likewise, the indicator of the confidence number may be numeric as in the example illustrated in FIG. 1, or it may be another type of graphical representation. The indicator may be a graphical magnitude bar whose length indicates the how big the confidence number is on a scale of from zero to one hundred in a graphical way without the use of numerals. In one example, the server 2 generates an entire graphical HTML document (web page) including the image 5, the first score 6, and the confidence number 7 or an indicator of the confidence number. The server 2 then serves that HTML document to the network-connected computer 3. A web browser executing on the network-connected computer 3 receives the HTML document from the server and causes the HTML document to be rendered on display 8. The result of what is displayed on display 8 is as depicted in FIG. 1.

Although the present invention has been described in connection with certain specific embodiments for instructional purposes, the present invention is not limited thereto. The example set forth above in connection with the diagrams is relatively simple and is set forth for illustrative purposes. The invention, however, is of general applicability and is not limited to details of this specific simple example. In another example, two different types of cell objects are identified by the tool, and the first score is a more complex function of both types of identified cell objects, and of distances between identified cell objects. In one example, the scoring procedure is that set forth in U.S. patent application Ser. No. 15/075,180, entitled "System for Predicting the Recurrence of Cancer in a Cancer Patient", filed Mar. 20, 2016, by Harder et al. (the entire subject matter of which is hereby incorporated by reference). Also, the manner of applying the overall false negative rate value is not limited to a simple reducing of one threshold value such that more cell objects will be identified in a cell identification process, and such that a cell candidate list is developed. In another example, the false negatives upon which the false negative rate value is based are not due to a failure of the tool to detect cell objects, but rather are due a failure of the tool to make another decision in the scoring process according to some a rule based on properly identified cell objects. In such a case, the novel method involves relaxing the rule so that multiple different precursor decisions could have been made that would have led to making the decision that should have been made. The second scores are generated by assuming that random different ones of these precursor decisions were made on each second pass, and then determining what the corresponding second score would have been had those particular precursor decisions been made.

For example, instead of the overall false negative rate value being due to a cell object identifying process not determining that enough cell objects exist in the image, the overall false negative rate value may be due to the identifying process not determining that enough cell objects of one type are close enough to a cell object of another type. The rule or threshold that is relaxed is not a "brown pixel value threshold", but rather is a threshold relating to a distance between cell objects when the "close enough" decision is made. When this threshold is relaxed, more cell objects will be determined to meet the "close enough" rule. A candidate list is prepared by determining certain precursor decision scenarios that now meet the rule but that with the unrelaxed threshold did not meet the rule. That a particular cell object is determined to be "close enough" to another cell object is such a precursor decision scenario. After the candidate list is prepared, a number of these precursor decision scenarios is randomly chosen as existing, and a second score is determined. Then another set of this number of precursor decision scenarios is randomly chosen as existing, and another second score is determined. The resulting second scores are then used, according to some function, to determine the confidence number.

Although the specific example set forth above in connection with the diagrams involves applying an overall false negative rate value and the above-described adding step, and also involves applying an overall false positive rate value and the above-described subtracting step, each second score is determined in another example without applying both adding and subtracting steps.

In the specific example set forth above in connection with the diagrams the adding step involves adding cell objects from a cell candidate list. Of all possible cell object sites in the image, the cell objects set forth in the cell candidate list are only those cell objects that meet certain criterion. In the example above, it is explained how the "brown pixel value threshold" is relaxed so that more cell objects will be identified. The cell objects in the cell candidate list are those cell objects that are newly identified as a result of this threshold relaxing process. The sites of the candidate cell objects are therefore not on a regular grid. It has been empirically determined, however, that the tool functions well or perhaps even better when there is no such criterion. Rather, the digital image is divided into a regular grid of square areas. If a particular square does not contain an identified cell object on the first pass, then the center of that square is identified as a candidate site where an added cell object can be placed in the adding step. Which particular ones of these candidate sites will be used in a second pass when cell objects are added is random. The number of cell objects added in the determination of a second score is the first number. The first number, as described above, is calculated from the overall false negative rate value. In yet another example, the cell candidate sites are determined by application of a Poisson disk sampling algorithm.

Although the function for determining the confidence number in the specific example set forth above in connection with the diagrams is a relatively simple one, the confidence number may be determined using a more complex function. For example, the impact of a particular second score on the confidence number being determined can be weighted according to the difference between the second score considered and the first score. If the difference between a second score and the first score is small, then the impact of this particular second score on the confidence number being determined is discounted, whereas if the difference between the particular second score and the first score is large, then the impact of this particular second score on the confidence number being determined is emphasized. In such a case, the confidence number is a scaled weighted sum. The weighted sum is a weighted sum of the second scores.

Although the specific example described above in connection with the diagrams involves applying a cell identification procedure to identify cell objects across the entire digital image, and then adding cell objects throughout that digital image based on a single overall false negative rate value number, and then subtracting cell objects from throughout the entire digital image based on a single overall false positive rate value number, in other embodiments the cell identification procedure is performed on multiple regions of the digital image. Cell objects are added and subtracted within each region separately based on potentially different overall false negative and overall positive rate value numbers. In such an embodiment, the "overall false negative rate value" is actually a composite of multiple sub-values. There is a first sub-value for situations in which the computerized cell identification procedure identified a first number of cell objects in a certain sized region of the image (a first identified cell object density), and there is a second sub-value for situations in which the computerized cell identification procedure identified a second number of cell objects in a certain sized sub-region of the image (a second identified cell object density), and there is a third sub-value for situations in which the computerized cell identification procedure identified a third number of cell objects in a certain sized sub-region of the image (a third identified cell object density), and so forth. Likewise, the "overall false negative rate value" is actually a composite of multiple sub-values.

Consider an example in which there are two regions of the digital image. In step 203, the tool identifies cell objects in the first region and generates a list. The tool also identifies cell objects in the second region and generates another list. These two lists are referred to together as the "first information". In steps 206 and 207, cell objects are added to and subtracted from the first region in accordance with the appropriate sub-value of the "overall false negative rate value" and in accordance with the appropriate sub-value of the "overall false positive rate value". If, for example, in step 203 the computerized cell identification procedure identified cell objects to have a first cell object density in the first region, then the false negative rate sub-value for situations of this identified cell object density is chosen to be the sub-value used in step 206. The false positive rate sub-value for situations of this identified cell object density is the appropriate sub-value to use in step 207. Steps 206 and 207 are applied on a region by region basis, separately. The result of steps 206 and 207 is a second list of cell objects for the first region, and a second list of cell objects for the second region. Both of these two second lists together are the "second information".

Next, to determine a second score in step 208, the scoring procedure is applied on the "second information". In a simple case, a highest cell object count is determined for the first region. It is the highest cell object count of any 50 micron by 50 micron square in the first region. Also, a highest cell object count is determined for the second region. It is the highest cell object count of any 50 micron by 50 micron square of the second region. These two highest cell object counts are then converted into a second score. In one example, the highest of the two highest cell object counts is mapped into a second score value as described above in connection with the simple case. In this embodiment, even though two different regions are actually considered for adding and subtracting cell objects, there is one resulting second score generated per pass through steps 206, 207 and 208. In step 210, the tool takes these second scores and generates the one confidence number from them. This one confidence number is the confidence number for the entire digital image. In step 211, the one confidence number is displayed to the user along with the one first score determined in step 205.

In another example, the overall false negative rate is a function that maps false negative rates to the density of detected cells, and the overall false positive rate is a function that maps false positive rates to the density of detected cells. The number of cells (cell objects) added or subtracted in a region of the image through steps 206 and 207 is dependent on the result of this function. The number of cells (cell objects) added or subtracted through steps 206 and 207 can also be determined for the whole image through a sliding window based on cell densities.

In another example, information about the variance of the false positive rate and the false negative rate are stored together with the overall false positive rate and overall false negative rate. This information is used in steps 206 and 207 to determine the number of cells to be added or to be removed based on both the overall rates and the variance. In another example, objects other than cells are detected (e.g. tumor glands) and the described method is applied to these objects.

Figure 9:
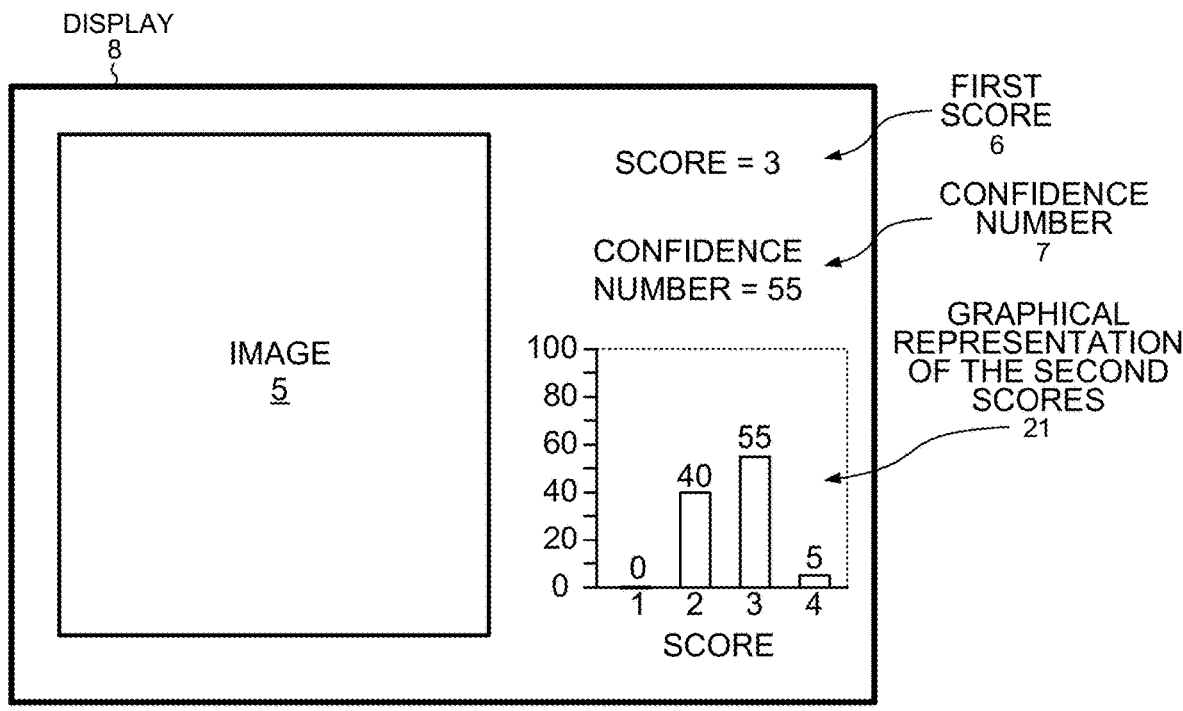
FIG. 9 illustrates one way that the first score, the confidence number, and a graphical representation of the second scores can be displayed on the display of the cancer scoring tool.

FIG. 9 is a diagram that illustrates another example of how information may be displayed by the cancer scoring tool 1 on the display 8. The cancer scoring tool 1 displays the digital image 5, the first score 6, the confidence number 7, as well as a graphical representation 21 of the second scores. All this information is displayed on display 8 at the same time. In the illustrated situation, fifty-five of the one hundred second scores exactly match the first score 6. By the manner of determining a confidence number set forth above, the confidence number 7 is 55. Five of the second scores had a score of 4. Forty of the second scores had a score of 40. None of the second scores had a score of 1. The number of second scores having each of the possible score values (1, 2, 3, 4) is set forth in the graphical representation 21. For each possible score value, a vertical bar is presented. The length of this bar indicates, and corresponds to, the number of second scores that had this possible score value. The second score values are indicated along the horizontal axis, whereas the number of second scores are indicated along the vertical axis.

Accordingly, various modifications, adaptations, and combinations of various features of the described embodiments can be practiced without departing from the scope of the invention as set forth in the claims.

What is claimed is:

1. A method involving a cancer scoring tool, the method comprising:
   (a) storing a false negative rate value and a false positive rate value for cell objects in the tool;
   (b) receiving a digital image into the tool, wherein the digital image is an image of a tissue sample of a cancer patient;
   (c) analyzing the digital image using a computerized cell identification procedure and thereby identifying a plurality of cell objects, wherein the false negative rate value and the false positive rate value are error rates at which the computerized cell identification procedure improperly fails to identify particular cells as being cell objects and falsely identifies particular cells as being cell objects;
   (d) storing first information, wherein the first information stored in (d) is indicative of the plurality of cell objects identified in (c);
   (e) applying a scoring procedure on the first information thereby determining a first score;
   (f) adding a first number of cell objects to the plurality of cell objects identified in (c), wherein the first number is determined based on the false negative rate value;
   (g) subtracting a second number of the cell objects identified in (c), wherein the second number is determined based on the false positive rate value;
   (h) storing second information, wherein the second information stored in (h) is indicative of the plurality of cell objects identified in (c) as added to in (f) and as subtracted from in (g);
   (i) applying the scoring procedure on the second information thereby generating a second score;
   (j) repeating (f), (g), (h) and (i) a plurality of times, wherein at least some of the particular cell objects that are added in (f) and the particular cell objects that are subtracted in (g) are different each time, and wherein each time another second score is generated in (i) such that a plurality of second scores is determined;
   (k) determining a confidence number based on the plurality of second scores determined in (j); and
   (l) storing the confidence number in association with the first score on the tool, wherein (a) through (l) are performed by the tool.

2. The method of claim 1, further comprising:
   (m) communicating an indicator of the confidence number and an indicator of the first score across a network.

3. The method of claim 2, wherein the indicator of the confidence number that is communicated in (m) is a number, and wherein the indicator of the first score that is communicated in (m) is a number.

4. The method of claim 2, wherein the communicating of (m) is a transmission of the confidence number and the first score as part of one or more network packets.

5. The method of claim 2, wherein the indicator of the confidence number and the indicator of the first score are communicated as part of an HTML document.

6. The method of claim 1, further comprising:
   (m) displaying both an indicator of the confidence number as well as an indicator of the first score on a display of the tool.

7. The method of claim 1, further comprising:
   (m) causing both an indicator of the confidence number as well as an indicator of the first score to be displayed on a display.

8. The method of claim 7, wherein the indicator of the confidence number that is displayed on the display in (m) is a number.

9. The method of claim 7, wherein the indicator of the confidence number that is displayed on the display in (m) is a graphical representation of a magnitude of the confidence number, and wherein the graphical representation does not include any numeral.

10. The method of claim 1, wherein the cell objects identified in (c) are a plurality of a cell objects of a first cell type, wherein (c) also involves identifying a plurality of cell objects of a second cell type, wherein the first information stored in (d) includes information indicative of the plurality of cell objects of the first cell type and also includes information indicative of the plurality of cell objects of the second cell type, and wherein the first score is determined in (e) based at least in part on the information indicative of the plurality of cell objects of the first type and also at least in part on the information indicative of the plurality of cell objects of the second type.

11. The method of claim 1, wherein the first information stored in (d) includes, for each cell object identified in (c), a cell object identifier and position information.

12. The method of claim 1, wherein the digital image received in (c) is a file, and wherein the file includes pixel data acquired by a slide scanning device.

13. The method of claim 1, wherein the scoring procedure involves determining a density of cell objects in a plurality of areas of the digital image.

14. The method of claim 1, wherein the adding of (f) involves adding a cell object indicated in a cell candidate list, wherein the cell candidate list is a list that identifies a plurality of potential cell objects, and for each identified potential cell object includes position information.

15. The method of claim 1, wherein the first score is a number the magnitude of which is indicative of the severity of cancer in the tissue sample and/or is indicative of the probability of success of a particular treatment and/or is indicative of a cancer sub-type.

16. A cancer scoring tool, comprising:
a port via which the tool receives a digital image, wherein the digital image is an image of a tissue sample;
a display upon which the tool displays a score and an indication of a confidence number, wherein the score is indicative of the severity of cancer in the tissue sample, and wherein the confidence number is associated with the score; and
means for determining the score and the confidence number by analyzing the digital image, wherein the means stores a false positive rate value and a false negative rate value and determines the confidence number based on the false positive rate value and the false negative rate value, wherein the false negative rate value and the false positive rate value are error rates at which a computerized cell identification procedure of the tool improperly fails to identify particular cells as being cell objects and falsely identifies particular cells as being cell objects.

17. The cancer scoring tool of claim 16, wherein the false positive rate value is a composite value involving multiple sub-values, and wherein the false negative rate value is a composite value involving multiple sub-values.

18. The cancer scoring tool of claim 16, wherein the means determines the confidence number by:
(a) analyzing the digital image using the computerized cell identification procedure and thereby identifying a plurality of cell objects;
(b) storing first information, wherein the first information stored in (b) is indicative of the plurality of cell objects identified in (a);
(c) applying a scoring procedure on the first information thereby determining a first score, wherein the first score is the score displayed on the display of the tool;
(d) adding a first number of cell objects to the plurality of cell objects identified in (a), wherein the first number is determined based on the false negative rate value;
(e) subtracting a second number of the cell objects identified in (a), wherein the second number is determined based on the false positive rate value;
(f) storing second information, wherein the second information stored in (f) is indicative of the plurality of cell objects identified in (a) as added to in (d) and as subtracted from in (e);
(g) applying the scoring procedure on the second information thereby generating a second score;
(h) repeating (d), (e), (f) and (g) a plurality of times, wherein at least some of the particular cell objects that are added in (d) and the particular cell objects that are subtracted in (e) are different each time, and wherein each time another second score is generated in (g) such that a plurality of second scores is determined; and
(i) determining the confidence number based on the plurality of second scores determined in (h), wherein (a) through (i) are performed by the means.

19. The cancer scoring tool of claim 16, wherein the tool comprises a server and a network-connected computer, wherein the port and the means are parts of the server, and wherein the display is a part of the network-connected computer.

20. A method involving a cancer scoring tool, the method comprising:
(a) storing false negative rate values and false positive rate values in the tool;
(b) receiving a digital image into the tool, wherein the digital image is an image of a tissue sample;
(c) analyzing a subset of the digital image using a computerized object identification procedure and thereby identifying a plurality of objects, wherein the false negative rate values and the false positive rate values are error rates at which the computerized object identification procedure improperly fails to identify particular cells as being objects and falsely identifies particular cells as being objects;
(d) storing first information, wherein the first information stored in (d) is indicative of the plurality of objects identified in (c);
(e) applying a scoring procedure on the first information thereby determining a first score;
(f) adding a first number of objects to the plurality of objects identified in (c), wherein the first number is determined based on the false negative rate values;
(g) subtracting a second number of the objects identified in (c), wherein the second number is determined based on the false positive rate values;
(h) storing second information, wherein the second information stored in (h) is indicative of the plurality of objects identified in (c) as added to in (f) and as subtracted from in (g);
(i) applying the scoring procedure on the second information thereby generating a second score;
(j) repeating (f), (g), (h) and (i) a plurality of times, wherein at least some of the particular objects that are added in (f) and the particular objects that are subtracted in (g) are different each time, and wherein each time another second score is generated in (i) such that a plurality of second scores is determined;
(k) determining a confidence number based on the plurality of second scores determined in (j); and
(l) storing the confidence number in association with the first score on the tool, wherein (a) through (l) are performed by the tool.

21. The method of claim 20, wherein a function F1 maps the number of detected objects to false negative rates or a false negative rate distribution, wherein a function F2 maps the number of detected objects to false positive rates or a false positive rate distribution, and wherein the function F1 is used to determine the number of objects to be added in step (f) and the function F2 is used to determine the number of objects to be added in step (g).

22. The method of claim 20, wherein a function F1 maps local image characteristics to false negative rates or a false negative rate distribution, wherein a function F2 maps local image characteristics to false positive rates or a false positive rate distribution, and wherein the function F1 is used to determine the number of objects to be added in step (f) and function F2 is used to determine the number of objects to be added in step (g).

23. The method of claim 20, wherein step (a) further involves storing a typical local object distribution in the tool, wherein this typical local object distribution is used in step (f) to determine potential object locations.

24. A method for generating a confidence interval using a cancer scoring tool, wherein the confidence interval is an interval for a histopathological score of a tissue section of a cancer patient, the method comprising the steps of:
(a) acquiring a region from a digital slide of the tissue section, wherein a specific protein of the tissue section is stained;

(b) detecting a first set of cell objects in the digital slide using a digital image analysis module, wherein the cell objects represent cells in the tissue section that express the protein;
(c) acquiring a dataset that represents statistical information on how the cell detection of the digital image analysis module compares to manually annotated cells;
(d) counting the number of cell objects in the first set;
(e) generating a set of scores by iterating the steps (f) through (j) until a predetermined condition is met;
(f) determining a first value N1 that represents a first fraction of the count of cell objects in the first set, wherein the first fraction is related to the false negative rate in the statistical information dataset;
(g) determining a second value N2 that represents a second fraction of the count of cell objects in the first set, wherein the second fraction is related to the false positive rate in the statistical information dataset;
(h) generating a second set of new cell objects comprising N1 new cell objects having coordinates within the region of the digital image;
(i) adding N2 randomly chosen cell objects from the first set to the second set;
(j) determining a histopathological score from the cell objects in the second data set and adding the histopathological score to the set of scores; and
(k) generating the confidence interval for the histopathological score from the set of scores and saving it to a persistent storage medium, wherein (a) through (k) are performed by the cancer scoring tool.

* * * * *